United States Patent [19]

Forsström et al.

[11] Patent Number: 5,382,908
[45] Date of Patent: Jan. 17, 1995

[54] CONDUCTIVITY OR CAPACITY CELL AND A METHOD FOR PRODUCING THE SAME AND A PROBE INCLUDING SUCH A CELL AND A METHOD FOR MEASURING OF RELATIVE HUMIDITY WITH SUCH A PROBE

[75] Inventors: Bo G. Forsström, Stockholm; Per E. Wikefeldt, Järfälla; Leif A. Unruh, Malmö, all of Sweden

[73] Assignee: Bo Gosta Forsstrom, Stockholm, Sweden

[21] Appl. No.: 761,870

[22] PCT Filed: Mar. 20, 1990

[86] PCT No.: PCT/SE90/00178

§ 371 Date: Sep. 11, 1991

§ 102(e) Date: Sep. 11, 1991

[87] PCT Pub. No.: WO90/11513

PCT Pub. Date: Oct. 4, 1990

[30] Foreign Application Priority Data

Mar. 20, 1989 [SE] Sweden .................. 8900979

[51] Int. Cl.⁶ .............................. G01N 27/07
[52] U.S. Cl. .................. 324/439; 324/450; 324/722; 204/400; 204/430; 174/11 R; 174/27
[58] Field of Search ............. 324/439, 450, 658, 686, 324/691, 722; 204/400, 430, 431; 174/11 R, 27

[56] References Cited

U.S. PATENT DOCUMENTS

| | | |
|---|---|---|
| 2,056,085 | 9/1936 | Alles .................. 324/439 X |
| 2,814,666 | 11/1957 | Maddox .................. 174/27 |
| 4,206,632 | 6/1980 | Suzuki .................. 174/11 R |
| 4,216,787 | 8/1980 | Hasenbeck .................. 324/696 X |
| 4,513,608 | 4/1985 | Cuming .................. 324/696 X |
| 4,570,477 | 2/1986 | Sugibuchi .................. 174/11 R |
| 4,696,184 | 9/1987 | Fukumoto et al. .................. 324/439 X |
| 4,954,238 | 9/1990 | Kato et al. .................. 204/430 |
| 5,087,886 | 2/1992 | Mann .................. 324/696 |
| 5,235,286 | 8/1993 | Masia et al. .................. 174/11 R X |

FOREIGN PATENT DOCUMENTS 2822769 9/1984 Germany .
375395 4/1975 Sweden .

Primary Examiner—Kenneth A. Wieder
Assistant Examiner—Glenn W. Brown
Attorney, Agent, or Firm—Young & Thompson

[57] ABSTRACT

Cell (19) for measuring moisture content of a material, comprising a sock (13) which is comprised of a plurality of braided threads, each thread consisting of a plurality of fibers comprised of an electrically non-conductive material. The sock is perfused with a moisture absorbing fluid. The sock comprises at least two electrodes (15, 17) in the form of wires comprised of a conducting material. These electrodes are braided as longitudinal threads in the sock (13). The electrodes are spaced from each other and extend essentially parallel to each other, the sock (13) being braided around a cylindrical core (11) comprised of an electrically non-conducting material. The axis of the core is essentially parallel to the electrodes (15, 17) and the threads in the sock (13) are permanently under tension to achieve contact between the threads and the electrodes (15, 17).

12 Claims, 3 Drawing Sheets

CONDUCTIVITY OR CAPACITY CELL AND A METHOD FOR PRODUCING THE SAME AND A PROBE INCLUDING SUCH A CELL AND A METHOD FOR MEASURING OF RELATIVE HUMIDITY WITH SUCH A PROBE

FIELD OF THE INVENTION

The invention relates to a conductivity or capacitivity cell and a method of manufacturing such a cell. The invention also relates to a sensor and a reference sensor for measuring the relative moisture content of a material, preferably concrete, by using such cells, and a method for measuring the relative moisture content using such a sensor and a reference sensor.

BACKGROUND OF THE INVENTION

When measuring the relative moisture content, cells of different types are used. For example, cells are used for measuring the relative moisture content in building construction, when it is necessary to determine when in situ concrete is sufficiently dry to be able to put a covering on the concrete, for example, without risk of moisture and/or mould damage. When using known cells for measuring the relative moisture content, problems have arisen with the accuracy of the cells. Known cells can undergo changes after calibration without this being noticed, or they can be inadvertently read before a vapour balance between the cell and the concrete has been reached. In some cases, the accuracy is so poor that use is limited to sensing free water in the vicinity of the cell. This is for example the case when using the device described in Swedish Application B-375395.

When measuring the relative moisture content of concrete, it is desirable that measuring error does not exceed one percentage unit within the measuring range 85–98% relative moisture. This cannot be achieved with previously known cells, because the accuracy of these cells is too low to achieve this. Furthermore, significant measuring errors can be caused by the fact that insertion of sensors with known cells in the concrete changes the temperature in the concrete.

The purpose of the present invention is to provide a conductivity or capacitivity cell of the type described by way of introduction which fulfills the accuracy requirement specified above, and a method of producing such a cell, which makes it possible to manufacture simply and inexpensively a large number of cells with very little variation as regards properties.

Another purpose of the invention is to provide a sensor for measuring the relative moisture content of a material, preferably concrete, said sensor using a cell according to the invention to achieve the desired accuracy, and a method for measuring the relative moisture content of a material to a desired accuracy.

BRIEF DESCRIPTION OF THE DRAWINGS

The invention will be described in more detail below with reference to the accompanying drawings, of which

DETAILED DESCRIPTION OF THE INVENTION

Figure 1:
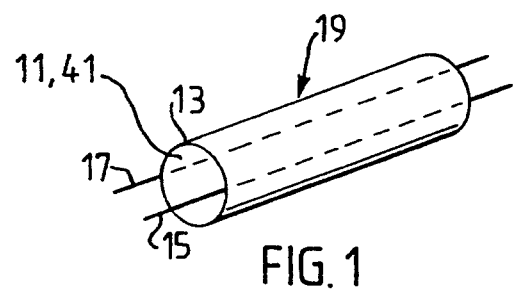
FIG. 1 is a perspective view of a conductivity or capacitivity cell according to the invention.

FIG. 1 shows a conductivity or capacitivity cell according to the invention. It comprises a cylindrical, for example circular cylindrical, possible tubular core 11 of an electrically non-conducting and moisture insensitive material, e.g. polypropylene. The core 11 is surrounded by a sock 13, which is braided from threads of an electrically non-conducting, elastic, relatively form-stable and moisture insensitive material, e.g. polypropylene. Along two diametrically opposite generatrices of the core 11, there extend two electrodes 15 and 17 of a relatively corrosion resistant and electrically conducting material, e.g. silver. The two electrodes 15 and 17 are braided into the sock 13 and constitute warp threads therein. The core 11, the sock 13 and the electrodes 15 and 17 form together a cell 19 according to the invention, which cell can be connected to a double-pole electrical sleeve terminal.

In use, the sock 13 is perfused with a carefully determined amount of a fluid which changes its properties as a result of a change in the relative humidity of the surrounding air. For a conductivity cell, the fluid can be for example a salt solution, which emits or absorbs moisture from the surrounding air until it achieves a vapour balance. When selecting a salt solution, the solution should not have any crystals within the measuring range in question. Furthermore, its conductivity should increase rapidly with increasing relative humidity. If the cell is a capacitivity cell, the fluid should be electrically non-conducting, e.g. a glycerol solution.

The core 11 can, for example, have a diameter of 4 mm and a length of 15 mm, the sock 13 having a thickness of, for example, 0.5 mm. The two electrodes 15 and 17 can, for example, have a diameter of 0.5 mm. The polypropylene fibers in the sock 13 can, for example, have a diameter of 30 μm.

Figure 3:
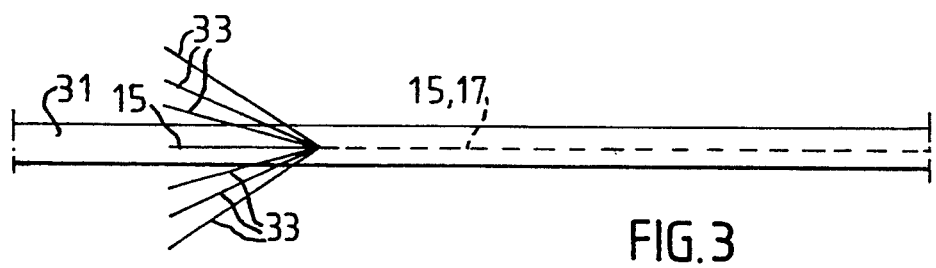
FIG. 3 is a schematic view showing the manufacturing of a work piece for a plurality of cells according to the invention.
Figure 4:
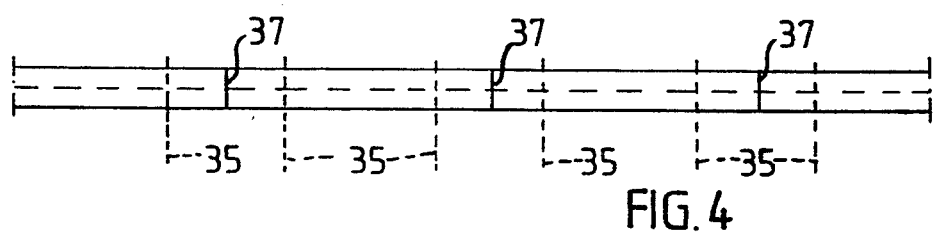
FIG. 4 is a schematic view, showing how the work piece is cut into blanks for cells.
Figure 5:
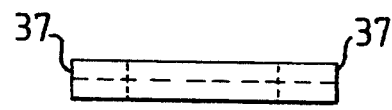
FIG. 5 shows a blank for a cell according to the invention.
Figure 6:
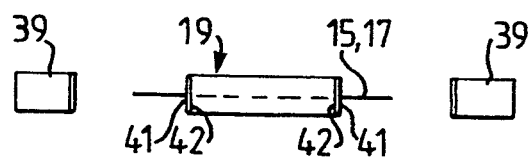
FIG. 6 shows the finished cell according to the invention after removing the end portions of the blank.

The cell 19 shown in FIG. 1 is manufactured in the following manner (see FIGS. 3–6). A number of threads 33, each containing a number of fibers of polypropylene, are braided as shown in FIG. 3 into a sock on a core work piece 31. At the same time, two electrodes 15 and 17 are braided into the sock as two longitudinal warp threads. The core work piece 31 and the sock braided thereon, as well as the braided-in electrodes, form a starting work piece for a plurality of cells 19, one of which is shown in FIG. 1. In the method shown in FIG. 4, the work piece is cut essentially perpendicular to its longitudinal direction with the aid of laser beams 35, which cut the core work piece 31 and the sock 13 but not the electrodes 15 and 17. At the same time, the cut-off ends of the sock are fused to the core on either side of the cut. The work piece is also cut-through completely at regular intervals as shown at 37. In this way, blanks are formed as shown in FIG. 5, from which there are removed the portions 39 which are formed between the cuts 37 and the laser cuts 35. After removal of the portions 39, the electrodes 15 and 17 are free at the ends 41, leaving the finished cell 19 as shown in FIG. 1.

According to the invention, the threads 33 in the sock 13 are longitudinally pre-tensioned in the cell 19, and this pre-tensioning can be achieved during braiding with the aid of the braiding machine or by shrinking the sock 13 with the help of heat treatment after braiding. The pre-tensioning provides the suitable contact pressure between the threads of the sock 13 and the electrodes 15 and 17. During cutting with the laser beam 35, the ends of the sock 13 are fused to the core 11 of each cell 19, so that the pre-tensioning of the threads is preserved.

Perfusion of the sock 13 with fluid can be done either directly in connection with the manufacture of the cell 19 or later, for example as the cell 19 is prepared for use. During perfusion, it is essential that the fluid be distributed evenly and reproduceably in the sock 13. This is the case if the fibers in the threads making up the sock 13 have a surface which is easily wetted by the fluid. The ends 41 and the fuse joints 42 of the cell (see FIG. 6) must, on the other hand, be fluid repellent to prevent the solution from seeping away from the sock. Polymers insensitive to moisture, such as polypropylene, have, as a rule, a strong water repellent surface, and therefore surface treatment, for example oxidation, is required of the original work piece prior to cutting with the laser beams 35, so that the fibers will be wettable. This treatment will not affect the end surfaces and the fuse joints, which have as yet not been created, and thus one will automatically achieve the result that the end surfaces and the fused joints will be water repellent. The treatment also affects the lateral outer surface of the core 11, which is advantageous.

In order to achieve strong and fluid-tight fuse joints 42, it can be necessary to have each of the laser beams 35 consist of a plurality of laser beams, lying in the cutting plane, thereby assuring that all of the threads in the sock 13 will be fixed in the fused joints. The electrodes 15 and 17 will thereby also be embedded in the fused joints, so that said joints will prevent fluid from seeping out of the sock 13 along the electrodes 15 and 17.

The method of manufacture described above in accordance with the invention assures that a plurality of cells 19, taken from the same batch, will be very uniform with each other. It can therefore be of practical value to provide each cell 19 with a marking identifying the batch. Such a marking can be arranged by the threads 33 having different colours, thus providing a colour code. Each thread spool in the braiding machine corresponds to one position in sock 13 and the colour of each thread spool can be selected as needed. The colour of the core 11 can also be a part of the colour code.

When using a conductivity cell 19 according to the invention, produced in the above-described manner, the resistance between the wires 15 and 17 will vary depending on the amount of fluid in the sock 13. If an A.C. voltage with a frequency of for example 1 kHz is applied across the electrodes 15 and 17, the resistance measured between the wires is a measure of the relative humidity in the air surrounding the conductivity cell 19, when there is vapour balance between the conductivity cell 19 and the surrounding area. Thus, the ends of the electrodes 15 and 17 comprise connector pins for connecting the conductivity cell 19 to a terminal, for example an electrical sleeve terminal of standard type. The ends of the electrodes 15 and 17 extending from the other end of the conductivity cell 19 can be used as gripping means for connecting the conductivity cell 19 to the sleeve terminal. This prevents the sock 13 from being touched and the electrodes 15 and 17 from being disturbed relative to the sock 13. The distance between the electrodes 15 and 17 is made equal to the distance between the sleeves in the electrical sleeve terminal.

Figure 2:
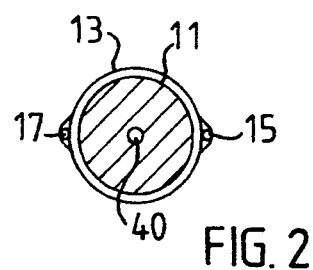
FIG. 2 shows a cross section through the cell according to claim 1.
Figure 7:
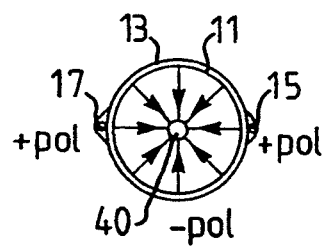
FIG. 7 shows an end surface of a cell according to the invention.

When the relative humidity is close to 100%, the volume of the fluid in the sock 13 will eventually be so great that it can no longer be held in the capillaries of the sock 13. Drops of liquid will fall from the sock 13 and measuring errors will occur, inter alia because the number of ions in the sock 13 will be reduced. If the conductivity cell 19 is mounted with the axis of the core 11 vertical, the lower end surface will thus be coated with solution, since the water repellent forces of the surface cannot overcome the weight of the fluid. It is thus essential for reliability to know if the end surfaces are coated with fluid or not. Detection of fluid on the surfaces of the ends 41 can be achieved with an extra wire 40 as shown in FIG. 2, embedded coaxially in the core 11. As long as the resistance between one or more electrodes 15 and 17 in the sock 13 and the electrode 40 in the core 11 is great, the end surface 41 is not coated with fluid. A radial electrical field thus scans the end surface 41 (see FIG. 7). The sock 13 with fluid has good conductivity.

Figure 8:
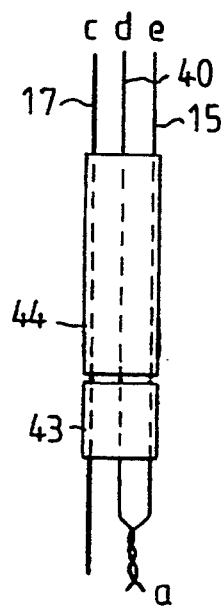
FIGS. 8a and 8b show a cell according to the invention provided with a drop detector.
Figure 8:
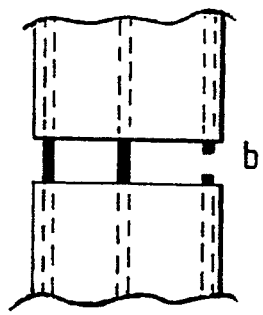

An alternative to the method with an electrode 40 in the core 11 is to use coloured fluid and a colourless drop detector 43 placed under the conductivity cell 19 (see FIG. 8). When a drop at 44 falls from the sock 13, it is caught by the drop detector 43, which is coloured as a signal that the conductivity cell 19 is to be replaced. A drop detector can for example be achieved by an extra laser cut somewhere between the ends 41 of the conductivity cell 19.

FIG. 8 also shows how the two methods can be combined. The electrode 40 is joined for example with the electrode 15 at a. The electrode 15 is also cut off at b. The resistance between the ends of the wires c and e is a measure of the relative humidity surrounding the conductivity cell 19. When a drop is caught, the drop detector 43 is coloured, and the resistance between the wire ends c and d drops considerably, these changes indicating independently of each other that the conductivity cell 19 must be replaced. The colouring of the drop detector 43 is retained even in dry air, since the fluid can have been converted into electrically non-conducting salt crystals, which are not electrically detectable.

Figure 9:
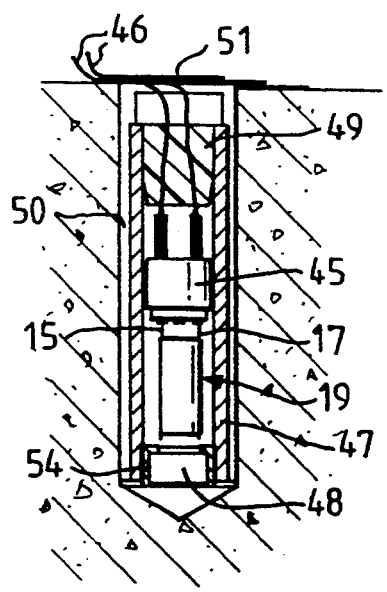
FIG. 9 shows a section through a sensor with a cell according to the invention embedded in concrete.

FIG. 9 shows a sensor for measuring the relative moisture content in concrete. The sensor comprises a conductivity cell 19 of the type described above, which is connected via its electrodes 15 and 17 to a sleeve terminal 45, which in turn is provided with output wires 46 for connection to a measuring instrument (not snown). The conductivity cell 19 and the sleeve terminal 45 are enclosed in a jacket 47, which in the embodiment shown is tubular and has at one end an opening 48. At the opposite end, the jacket 47 is closed by means of a plug 49, through which the wires 46 are led. The sensor is mounted in a cavity 50, in the concrete, and is sealed at the top by means of a cover 51. A sealing ring 54 at the inner end of the jacket 47 in the vicinity of the opening 48 prevents air from the surroundings from penetrating into the jacket 47 through the opening 48. It is also possible to fill the cavity 50 between the concrete and the jacket 47 with a sealing material to prevent air from the surroundings from penetrating into the cavity 50.

Via the opening 48, the space around the conductivity cell 19 in the jacket 47 communicates with the lower portion of the cavity 50. The air surrounding the conductivity cell 19 has a relative humidity which is dependent on the relative moisture content of the concrete, and in the matter described above, vapour balance will be established between the conductivity cell 19 and the surrounding air, so that the properties of the conductivity cell will be changed as a function of the changes in the relative moisture content of the concrete. The temperature of the concrete is not affected by the presence of the sensor.

Figure 10:
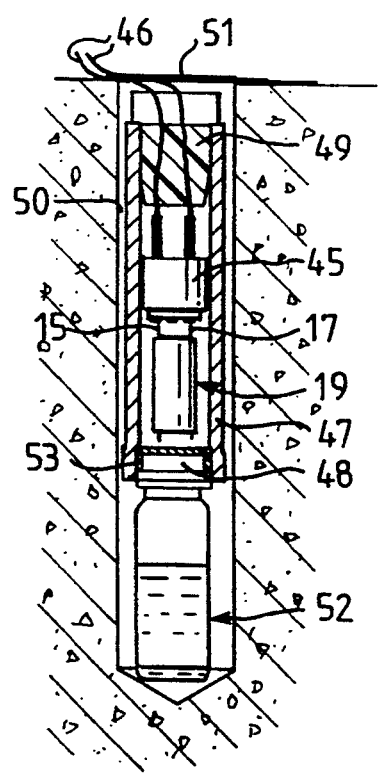
FIG. 10 shows a section through a reference sensor with a cell according to the invention embedded in concrete.

FIG. 10 shows a reference sensor for measuring the relative moisture content of concrete, and this reference sensor corresponds to the sensor shown in FIG. 9 with the exception that a container 52 is attached to the opening 48. The container 52 contains a fluid, preferably a saturated salt solution, which keeps the relative humidity of the air above the upper surface of the solution in the container 52 at the value which is to be achieved in the concrete. In this manner, the reference sensor provides a reference value which is very accurate as a result of the fact that the temperature of the reference sensor and the other sensors will be virtually identical.

When measuring the relative moisture content of the concrete, the conductivity values of the reference sensor and the other sensors are compared. The ratio between the conductivity values indicates the moisture of the concrete relative to the desired value. When the measured value from the reference sensor and another sensor are in agreement, the moisture content of the concrete has achieved the desired value.

In order to prevent dust, liquid, concrete and other foreign particles from penetrating into the jacket 47 of the sensor shown in FIG. 9, a filter (not shown) of polypropylene fibers, for example, can be arranged in the lower portion of the jacket 47 near the opening 48. In order to prevent fluid from the container 52 from seeping into the opening 48, a vapour permeable but fluid impermeable barrier 53 can be arranged in the opening 48.

We claim:

1. Cell (19) for measuring moisture content of a material, comprising a sock (13) which is comprised of a plurality of braided threads, each thread consisting of a plurality of fibers comprised of an electrically non-conductive material, said sock being perfused with a moisture absorbing fluid, said sock comprising at least two electrodes (15, 17) in the form of wires comprised of a conducting material, said electrodes being braided as longitudinal threads in the sock (13), wherein the electrodes are spaced from each other and extend essentially parallel to each other, the sock (13) being braided around a cylindrical core (11) comprised of an electrically non-conducting material, wherein the axis of the core is essentially parallel to the electrodes (15, 17) and the threads in the sock (13) are permanently under tension to achieve contact between the threads and the electrodes (15, 17).

2. Cell according to claim 1, wherein the sock (13) is fused to the core (11) at the ends (41) of the core, thereby to preserve said tension of said threads.

3. Cell according to claim 2, wherein the fibers in the sock (13) are water wettable on the outer surfaces of the fibers.

4. Cell according to claim 1, wherein the ends of the electrodes (15, 17) comprise connecting pins for connection with an electrical terminal.

5. Cell according to claim 1, wherein the color of each of the threads (33) in the sock (13) and the color of the core (11) form a color code for identifying the cell (19).

6. Sensor for measuring the relative moisture content of a material, comprising a jacket (47) adapted to be embedded in the material and having an opening (48) towards the material, and a cell (19) according to claim 1 disposed in the jacket.

7. Sensor according to claim 6, characterized in that a filter is arranged in the jacket (47) opening (48) towards the material in order to prevent foreign particles from penetrating into the jacket (47).

8. Reference sensor for measuring relative moisture content in a material, comprising a sensor in accordance with claim 6 and a container (52) connected to the opening (48) and opened towards the sensor, said container containing a fluid which keeps the relative humidity of the air in the container (52) and the sensor at a predetermined value.

9. Reference sensor according to claim 8, characterized in that a vapor permeable but fluid impermeable barrier (53) is disposed between the fluid in the container (52) and the cell (19).

10. Method of manufacturing a cell for measuring moisture content of a material, comprising braiding a sock from a plurality of threads, each consisting of a plurality of fibers of an electrically non-conducting material, said braiding being performed on a core work piece (31) of an electrically non-conducting material simultaneously with braiding into the sock at least two electrodes (15, 17) in the form of wires of an electrically conducting material as warp threads spaced from each other and essentially parallel to each other and with the axis of the core work piece, cutting the core work piece, together with the sock and the electrodes, transverse to the longitudinal direction of said core work piece into a number of sections and removing portions (39) of the core work piece and the sock from the ends of the section so as to expose the electrodes (15, 17), the sock during manufacture being perfused with a moisture absorbing fluid, and its threads being pre-tensioned to achieve contact between the threads and the electrodes.

11. Method according to claim 10, characterized in that the portions (39) are removed by means of at least one laser beam (35).

12. Method according to claim 10, characterized in that the sock (13) is perfused with the fluid by a capillary tube, containing the fluid for perfusing the sock.

* * * * *